(12) United States Patent  
Schmitz-Hübsch

(10) Patent No.: US 8,838,407 B2
(45) Date of Patent: Sep. 16, 2014

(54) NON-CONTACT FREEZING TEMPERATURE DETERMINATION

(75) Inventor: Axel Schmitz-Hübsch, Remseck (DE)

(73) Assignee: G. Lufft Meβ-Und Regeltechnik GmbH, Fellbach-Schmiden (DE)

( * ) Notice: Subject to any disclaimer, the term of this patent is extended or adjusted under 35 U.S.C. 154(b) by 435 days.

(21) Appl. No.: 12/853,474

(22) Filed: Aug. 10, 2010

(65) Prior Publication Data

US 2011/0040518 A1 Feb. 17, 2011

(30) Foreign Application Priority Data

Aug. 11, 2009 (EP) ..................................... 09010350

(51) Int. Cl.
*G01K 11/30* (2006.01)
*G01N 25/06* (2006.01)
*G01N 25/04* (2006.01)
*G08B 19/02* (2006.01)

(52) U.S. Cl.
CPC ................ *G01N 25/04* (2013.01); *G08B 19/02* (2013.01)
USPC ............................................ 702/135; 374/17

(58) Field of Classification Search
CPC ............ B60T 2210/12; B60G 2400/82; B60G 2400/8424; G01B 11/0625
USPC ....................... 702/135, 33, 40, 57, 130, 134; 250/493.1, 306, 307, 308; 324/92, 96, 324/105; 356/326; 374/100, 109, 159; 700/299
See application file for complete search history.

(56) References Cited

U.S. PATENT DOCUMENTS

| 5,619,193 | A | | 4/1997 | Doherty et al. |
| 5,774,070 | A | * | 6/1998 | Rendon ......................... 340/905 |
| 6,049,387 | A | * | 4/2000 | Griesinger .................... 356/419 |

(Continued)

FOREIGN PATENT DOCUMENTS

| DE | 4133359 | 4/1993 |
| EP | 0898147 | 2/1999 |

(Continued)

OTHER PUBLICATIONS

Turunen, "Measuring salt and freezing temperature on roads", 1997; Meteorol, pp. 11-15.*

(Continued)

*Primary Examiner* — Sujoy Kundu
*Assistant Examiner* — Ricky Ngon
(74) *Attorney, Agent, or Firm* — Michael Best & Friedrich LLP

(57) ABSTRACT

A method and device for determining the freezing temperature of an ice-water mixture on a road surface. Reference measurements of ice-to-water ratios in dependence on road temperatures for different salt contents of reference ice-water mixtures are provided to the device. The thickness of a water layer on the road surface is detected and the thickness of an ice layer of the road surface is detected by the device and method. From the detected thickness of the water layer and the detected thickness of the ice layer, an ice-to-water ratio of the ice-water mixture is determined. The temperature of the road surface is also detected. The freezing temperature of the ice-water mixture is determined by the device and method from the determined ice-to-water ratio and the detected temperature by means of the provided reference measurements.

17 Claims, 2 Drawing Sheets

(56) References Cited

U.S. PATENT DOCUMENTS

| | | |
|---|---|---|
| 6,166,657 A | 12/2000 | Mann |
| 6,459,083 B1 * | 10/2002 | Finkele et al. ............ 250/339.11 |
| 7,224,453 B2 * | 5/2007 | Elman ........................... 356/326 |
| 7,301,478 B1 * | 11/2007 | Chinn et al. ................... 340/905 |
| 2005/0167593 A1 * | 8/2005 | Forsyth .................... 250/339.11 |

FOREIGN PATENT DOCUMENTS

| | | |
|---|---|---|
| EP | 1602913 | 12/2005 |
| JP | 11229311 | 8/1999 |
| WO | 97/13234 | 4/1997 |

OTHER PUBLICATIONS

EP09010350 Search Report dated Dec. 16, 2009 (2 pages).

* cited by examiner

NON-CONTACT FREEZING TEMPERATURE DETERMINATION

FIELD OF THE INVENTION

The present invention relates to the determination of freezing temperatures on roads, and particularly to the non-contact determination of freezing temperatures by means of optical sensors.

BACKGROUND

In general, road salts are used in order to increase the road safety on winterly roads. An important parameter for the organization of winter road maintenance as well as for the required quantity of the road salt to be spread is the freezing temperature on the road. According to the prior art the freezing temperature is detected by a sensor system installed in the road. This sensor system comprises, for instance, electrodes by means of which the conductivity of the water or water-ice mixture on the road and, thus, the salt content is sensed. Then, based on the salt content, the freezing temperature is determined. According to another approach an aqueous salt solution is actively cooled, and the freezing temperature is determined on the basis of the detected enthalpy jump.

However, the installation and maintenance of the sensor system calls for a great amount of work and disruptions of the traffic flow due to the road closure required for the installation and maintenance. Moreover, the installed sensor system provides information about the freezing temperature merely locally and for a relatively small area.

The present invention is based on the object to overcome the aforementioned drawbacks of the conventional freezing temperature determination and to provide a local or non-local reliable freezing temperature determination on winterly roads.

SUMMARY

The aforementioned object is achieved with the method according to claim 1 and the device according to claim 8. Thus, there is provided a method for determining the freezing temperature of an ice-water mixture on a road surface, comprising: providing reference measurements of ice-to-water ratios in dependence on road temperatures for different salt contents of reference ice-water mixtures; determining an ice-to-water ratio of the ice-water mixture; detecting the temperature of the road surface; and determining the freezing temperature of the ice-water mixture from the determined ice-to-water ratio and the detected temperature by means of the provided reference measurements.

Thus, a thickness of a water layer (thickness of water) on a road and a thickness of an ice layer (thickness of ice) on the road can be detected, and the ice-to-water ratio of the ice-water mixture can be determined from the detected thickness of the water layer and the detected thickness of the ice layer.

Furthermore, there is provided a device for the (non-contact) determination of the freezing temperature of an ice-water mixture on a road surface, comprising a storage unit adapted to store reference measurement values of ice-to-water ratios in dependence on road temperatures for different salt contents of reference ice-water mixtures; a first sensor means adapted to detect the temperature of the road (road surface temperature); and a computing unit adapted to determine an ice-to-water ratio of the ice-water mixture, and to determine the freezing temperature of the ice-water mixture from the determined ice-to-water ratio (proportion of ice in the ice-water mixture), the detected temperature of the road and the stored reference measurement values.

Moreover, the device may comprise a second sensor means, which is adapted to detect a thickness of a water layer (thickness of water) on a road and a thickness of an ice layer (thickness of ice) on the road. In this case, the computing unit is adapted to determine the ice-to-water ratio of the ice-water mixture from the detected thickness of the water layer and the detected thickness of the ice layer.

The detection of the temperature of the road is, strictly speaking, carried out for the surface of the road. If, for reasons of simplification, the road will be referred to in various passages below, it shall be understood that the temperature of the road surface is measured, and that the thickness of the water layer/ice layer of the ice-water mixture on the road surface is measured. It is self-evident that the water layer/ice layer, whose thickness is detected, can consist of several layers, i.e. that the detected thickness corresponds to the total thickness of several water layers/ice layers present in the ice-water mixture. Particularly, the ice-water mixture will generally not include merely one homogenous water layer with one homogenous ice layer on top thereof or underneath it.

The freezing temperature is determined in such a way that no direct mechanical contact is necessary between the device, by means of which the freezing temperature on a road is determined, and the road surface. Specifically, the device according to the invention may be mounted on a vehicle, e.g. an automobile or truck, and the freezing temperature can be determined continuously or discontinuously along at least a portion of the road as the vehicle is driving along the road.

Contrary to the above-described prior art it is, therefore, possible to determine the freezing temperature of the ice-water mixture present on the road at many positions of the road in a mobile fashion. The installation and maintenance of the device do not necessitate any roadwork. The freezing temperature, i.e. the temperature at which the water of the ice-water mixture starts freezing/crystallizing, is reliably determined on the basis of measurement series conducted in advance, which establish a relation between the proportion, specifically the percentage, of ice in reference ice-water mixtures and different road temperatures, and for different salt contents of the reference ice-water mixtures. It is noted that the ice-water mixture according to the present application may, in principle, contain from 0 to 100% of ice.

According to an example, the step of determining the freezing temperature from the determined ice-to-water ratio and the detected road temperature by means of the provided reference measurements comprises the determination of the salt content of the ice-water mixture from the determined ice-to-water ratio and the detected road temperature by means of the provided reference measurements and the determination of the freezing temperature from the determined salt content and the provided reference measurements/reference measurement curves (for details, see description below, with reference to the drawing).

The thickness of the water layer and/or the thickness of the ice layer can be detected by means of optical sensors, and specifically by means of infrared spectroscopy. The temperature of the road can be detected by means of an infrared temperature sensor. In order to detect the water layer thickness/ice layer thickness devices as are known from DE 4133359 A1 may be used. Commercially available quotient pyrometers, narrow-band pyrometers or band radiation pyrometers may be used for the temperature measurement. Thus, the detection of the water layer thickness/ice layer thickness and, therefore, of the percentage of ice (ice percent)

as well as of the road temperature is possible in a non-contact fashion and reliably, with relatively little efforts.

Accordingly, the above-described inventive device can be provided in such a way that the second sensor means comprises at least one optical sensor and/or that the first sensor means comprises an infrared temperature sensor. The second sensor means may comprise an infrared spectroscopy apparatus. Moreover, the inventive device may comprise at least one light source, which is adapted to radiate light in a predetermined wavelength range, specifically in the infrared range. The light reflected by the road after having passed through the ice-water mixture is then detected. The light source can emit, for instance, a broadband light of a known spectrum. As the ice-water mixture absorbs the radiation in dependence on the wavelength, the analysis of the reflected light allows the determination of the thickness of the ice layer and the water layer. Here, the fact that the absorption bands of ice and water are different is made use of.

According to a further development the computing unit of the device is adapted to determine the salt content of the ice-water mixture from the determined ice-to-water ratio and the detected temperature with the aid of the stored reference measurement values, and to determine the freezing temperature from the determined salt content and the stored reference measurement values.

Additional features and an exemplary embodiment of the present invention shall be explained in more detail below by means of the drawing. It shall be understood that the embodiment does not exhaust the scope of the present invention.

DETAILED DESCRIPTION

Figure 1:
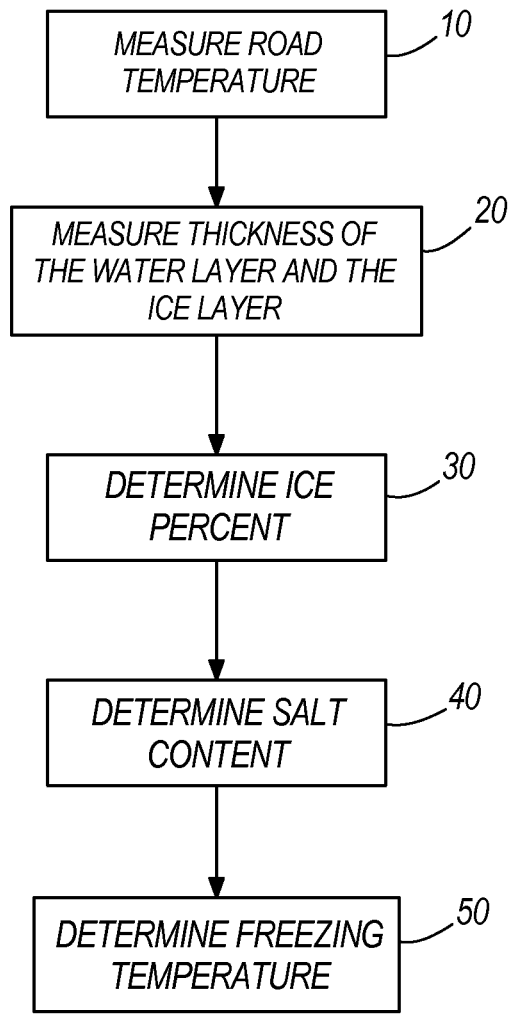
FIG. 1 represents a flow diagram, which serves to illustrate some steps of an exemplary embodiment of the method according to the invention.

As is shown in FIG. 1, the inventive method for the non-contact determination of a freezing temperature of an ice-water mixture on a road surface comprises the step of measuring the road temperature 10. In this step, specifically the thermal radiation of the road surface can be detected. Furthermore, the thickness of the water layer and the thickness of the ice layer are measured, 20. The measurement may be carried out by means of spectroscopy, for instance, in the near infrared range. For instance, light having wavelengths of 1450 nm and 1190 or 1080 nm can be emitted and the reflecting light can be detected, as is described in DE 4133359 A1. It shall be understood that the order of temperature measurement and thickness measurement is irrelevant. The percentage of ice (ice percent) in the ice-water mixture on the road can be determined directly from the ratio of the thickness of the water layer to the thickness of the ice layer, 30. It be mentioned one more time that no homogenous water layer/ice layer is assumed, but that the thickness of the water and ice present in the ice-water mixture on the road as a whole is determined. In doing so, specifically the total thickness of the ice present in the ice-water mixture and the total thickness of the water present in the ice-water mixture can be detected by means of filtering known, in principle, from the prior art, with filters having different wavelength sensitivities.

According to the embodiment described herein, the salt content/the salt concentration of the ice-water mixture is determined, 40, on the basis of the percentage of ice in the ice-water mixture determined in step 30. To this end, reference measurement values for reference ice-water mixtures established in advance are applied. These reference measurement values can be obtained as follows. A water-salt solution with a well-defined salt content is cooled down continuously. Upon reaching the freezing temperature first ice crystals are formed. The percentage of ice increases as temperatures continue to drop, until the originally liquid water-salt solution is ultimately completely frozen (100% ice percent). This functional, empirically obtained relation of ice percent and temperature is determined for a number of reference ice-water mixtures (in each case proceeding from completely liquid solutions) for different salt contents, and is provided as reference measurements.

In order to determine the real freezing temperature of the ice-water mixture on the road, the temperature controlled under controlled test conditions is set equivalent to the measured road temperature. The respective percentage of ice determined under controlled test conditions is set equivalent to the ice-to-water ratio, which was determined by means of the measured thickness of the water layer and the ice layer of the ice-water mixture on the road.

Figure 2:
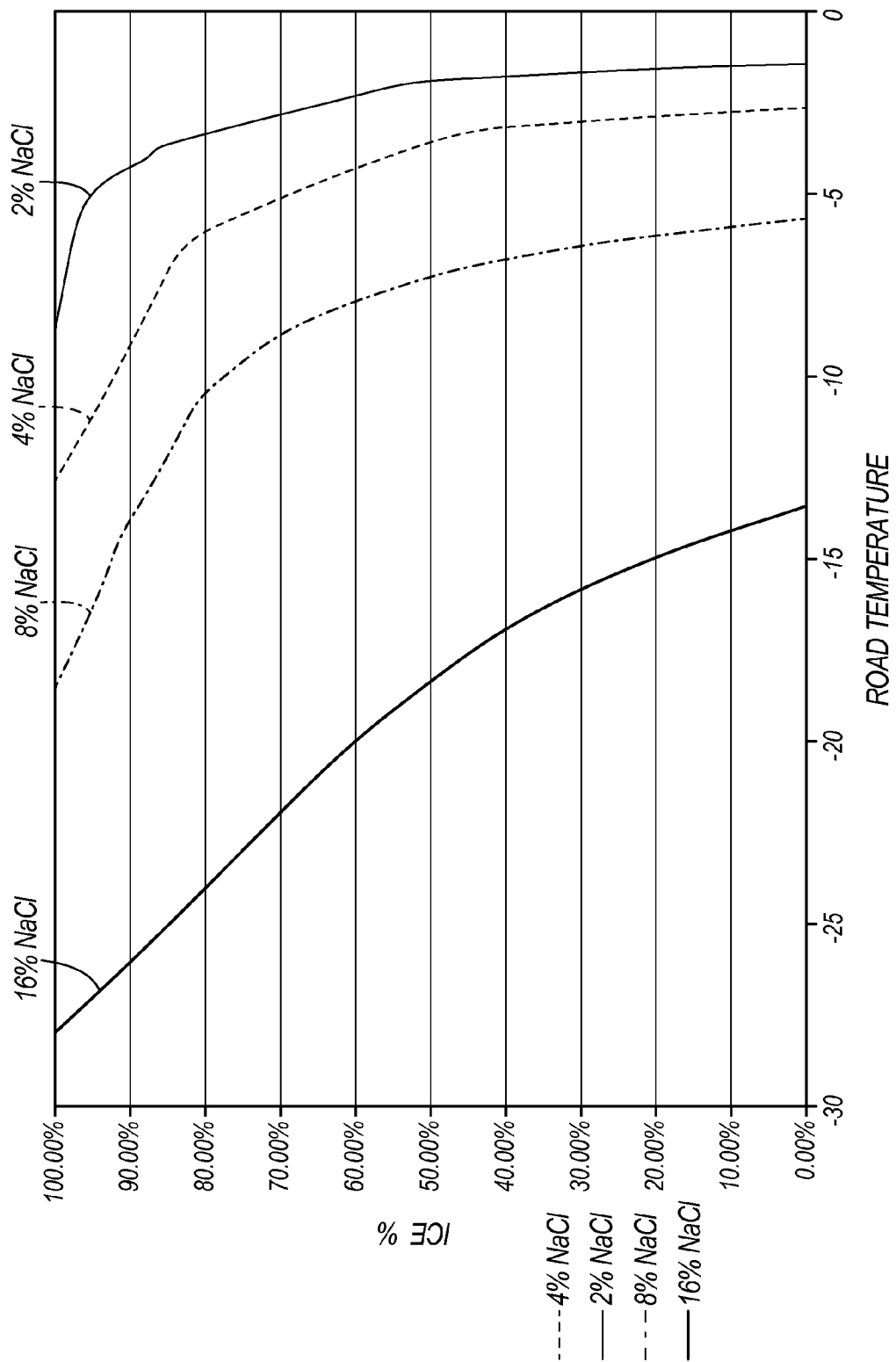
FIG. 2 shows reference curves of reference measurement values, which serve the inventive determination of the freezing temperature of an ice-water mixture on a road surface.

An example for reference measurement values is shown in FIG. 2, in the form of reference measurement curves for reference ice-water mixtures having different salt contents. The percentage of ice (ice percent) is plotted on the ordinate of the diagram of FIG. 2; the road temperature (equivalent to the temperature controlled under test conditions) is plotted on the abscissa of the diagram of FIG. 2. In the present example, measurement series of ice percent (from 0 to 100%) were conducted in dependence on the road temperature (from just under zero degrees Celsius to approximately −30 degrees Celsius) for a salt content (NaCl) of 2%, 4%, 8% and 16%.

As can be seen in FIG. 2, a salt content of 8% can be determined from the third measurement curve from the right (step 40 of FIG. 1) from a percentage of ice determined in step 30 of FIG. 1 of, for instance, approximately 50% and the road temperature measured in step 10 of FIG. 1 of, for instance, −6.8 degrees Celsius. In other words, a measurement curve, or a curve calculated by the interpolation of provided measurement curves/measurement series, and thus an associated salt content can be determined uniquely for each pair of ice percent and road temperature.

If the corresponding measurement curve is identified, or a corresponding curve is calculated by the interpolation of existing measurement curves, the associated freezing temperature corresponding to 0 ice percent can be read out/determined directly in step 50 of FIG. 1, exemplarily from FIG. 2. In the example chosen, thus a freezing temperature of approximately −5.3 degree Celsius is determined for a salt content of 8% corresponding to the pair of ice percent and road temperature.

What is claimed is:

1. A method for determining the freezing temperature of an ice-water mixture on a road surface, comprising:
  providing reference measurements of ice-to-water ratios in dependence on road temperatures for different salt contents of reference ice-water mixtures;
  determining an ice-to-water ratio of the ice-water mixture using a second sensor;
  detecting a temperature of the road surface using a first sensor;
  determining, by a computing unit, a salt content of the ice-water mixture from the determined ice-to-water ratio and the detected temperature by means of the provided reference measurements; and determining, by the computing unit, the freezing temperature of the ice-water mixture from the determined salt content and the provided reference measurements.

2. The method according to claim 1, further comprising:
detecting a thickness of a water layer on the road surface using the second sensor; and
detecting a thickness of an ice layer on the road surface using the second sensor;
and in which the ice-to-water ratio of the ice-water mixture is determined from the detected thickness of the water layer and the detected thickness of the ice layer.

3. The method according to claim 2, in which the thickness of the water layer and/or the thickness of the ice layer is detected by means of optical sensors.

4. The method according to claim 3, in which the thickness of the water layer and/or the thickness of the ice layer is detected by means of infrared spectroscopy.

5. The method according to claim 1, in which the temperature of the road surface is detected by means of an infrared temperature sensor.

6. The method according to claim 1, in which the freezing temperature is determined continuously or discontinuously along at least a portion of the road by means of a device attached to a vehicle, and wherein the method comprises moving the device along the road by moving the vehicle.

7. The method according to claim 1, wherein the reference measurements include data representing a plurality of measurement curves, and the step of determining the salt content of the ice-water mixture from the determined ice-to-water ratio and the detected temperature by means of the provided reference measurements comprises identifying one of the measurement curves corresponding to the determined ice-to-water ratio and the detected temperature.

8. The method according to claim 7, wherein the freezing temperature of the ice-water mixture is a data point on the identified measurement curve and the freezing temperature is determined by identifying the data point.

9. A device for determining the freezing temperature of an ice-water mixture on a road surface, comprising:
a storage unit adapted to store reference measurement values of ice-to-water ratios in dependence on road temperatures for different salt contents of reference ice-water mixtures;
a first sensor adapted to detect a temperature of the road surface; and
a computing unit adapted
to determine an ice-to-water ratio of the ice-water mixture,
to determine a salt content of the ice-water mixture from the determined ice-to-water ratio and the detected temperature by means of the stored reference measurement values, and
to determine the freezing temperature from the determined salt content and the stored reference measurement values.

10. The device according to claim 9, further comprising:
a second sensor adapted to detect a thickness of a water layer on a road surface and a thickness of an ice layer on the road surface; and in which
the computing unit is adapted to determine the ice-to-water ratio of the ice-water mixture from the detected thickness of the water layer and the detected thickness of the ice layer.

11. The device according to claim 10, in which at least one of the second sensor comprises at least one optical sensor and the first sensor comprises an infrared temperature sensor.

12. The device according to claim 11, in which the second sensor comprises an infrared spectroscopy apparatus.

13. The device according to one of claim 9, which comprises at least one light source adapted to radiate light in a predetermined wavelength range, specifically in the infrared range.

14. The device according to one of claim 9, wherein the device is adapted to be mounted on a vehicle, specifically an automobile or a truck.

15. A method for determining the freezing temperature of an ice-water mixture on a road surface, comprising:
providing reference measurements of ice-to-water ratios in dependence on road temperatures for different salt contents of reference ice-water mixtures, the reference measurements including data representing a plurality of measurement curves;
detecting a temperature of the road surface using a first sensor;
detecting a thickness of a water layer on the road surface using a second sensor; and
detecting a thickness of an ice layer on the road surface using the second sensor;
determining an ice-to-water ratio of the ice-water mixture from the detected thickness of the water layer and the detected thickness of the ice layer;
identifying one of the measurement curves corresponding to the determined ice-to-water ratio and the detected temperature;
determining, by a computing unit, a salt content of the ice-water mixture associated with the identified measurement curve; and
determining, by the computing unit, the freezing temperature of the ice-water mixture from the identified measurement curve.

16. The method according to claim 15, wherein the freezing temperature of the ice-water mixture is a data point on the identified measurement curve.

17. The method according to claim 15, wherein each of the plurality of measurement curves is associated with a different salt content.

* * * * *